United States Patent [19]

Chaussee

[11] Patent Number: 4,603,005
[45] Date of Patent: Jul. 29, 1986

[54] CLEANING COMPOSITIONS CONTAINING ALPHA OLEFIN/MALEIC ANHYDRIDE TERPOLYMERS

[75] Inventor: James G. Chaussee, Racine County, Wis.

[73] Assignee: S. C. Johnson & Son, Inc., Racine, Wis.

[21] Appl. No.: 672,964

[22] Filed: Nov. 19, 1984

[51] Int. Cl.$^4$ .................. C11D 3/37; C11D 17/08
[52] U.S. Cl. .................. 252/174.24; 252/173; 252/174.23; 252/549; 252/550; 252/552; 252/DIG. 2; 252/DIG. 5; 252/DIG. 13; 252/DIG. 14
[58] Field of Search ............ 252/174.24, 174.23, 252/DIG. 2, DIG. 3, DIG. 5, DIG. 13, DIG. 14; 526/272

[56] References Cited

U.S. PATENT DOCUMENTS 3,560,456  2/1971  Hazen ........................ 524/854
3,969,500  7/1976  Kennerley ............... 252/174.24
4,358,573  11/1982  Verbrugge ................. 526/272

FOREIGN PATENT DOCUMENTS 53198  5/1981  Japan .

Primary Examiner—Paul Lieberman
Assistant Examiner—Hoa Van Le

[57] ABSTRACT

This invention relates to the use of alpha olefin/maleic anhydride terpolymers in conjunction with anionic surfactants, such as ammonium lauryl sulfate and ammonium lauryl ether sulfate, in hair, skin and other cleaning compositions. The use of alpha olefin/maleic anhydride terpolymers in such cleaning compositions reduces the irritation potential of anionic surfactants without decreasing the foaming and cleaning characteristics of such compositions.

15 Claims, No Drawings

CLEANING COMPOSITIONS CONTAINING ALPHA OLEFIN/MALEIC ANHYDRIDE TERPOLYMERS

BACKGROUND OF THE INVENTION

This invention relates to the use of alpha olefin/maleic anhydride terpolymers in cleaning compositions. More particularly, this invention relates to the use of these terpolymers in conjunction with anionic surfactants, such as ammonium lauryl sulfate and ammonium lauryl ether sulfate, in hair shampoos, hand or skin cleaners and other cleaning compositions.

The use of anionic surfactants or detergents in skin and hair cleaning compositions is well known. Most of the major national brand liquid hand soaps contain sodium $C_{14-16}$ olefin sulfonate or sodium lauryl sulfate as the major anionic surfactant. Additionally, several major national brand shampoos contain ammonium lauryl sulfate, ammonium lauryl ether sulfate, or mixtures thereof. It is well-known and universally accepted that these compositions are irritating to the skin and eyes under many conditions of use. Nevertheless, anionic surfactants continue to be frequently used in cleaning compositions because of their superior foaming characteristics. These characteristics exist even when the anionic surfactants are present in relatively dilute amounts. It has long been desired to reduce or eliminate the irritability of such cleaning compositions without compromising their superior cleaning and foaming properties.

The alpha olefin/maleic anhydride terpolymers employed in the compositions of this invention are disclosed in Reexamination Certificate No. B1 4,358,573. These compounds are terpolymers because they are composed of two different alpha olefin monomers (herein described as a lower 1-alkene and a higher 1-alkene) and a maleic anhydride monomer. These terpolymers are described as waxy materials having a low viscosity, suitable for such end uses as mold release agents, slip agents and additives to floor polishes. This patent, however, does not disclose or suggest the use of these terpolymers in skin and hair cleaning compositions. Additionally, these terpolymers are generally poor foam producers when employed alone.

Various efforts to reduce the irritation of cleaning compositions, yet maintain the desired foaming properties, have been proposed. For example, certain commercial formulations eliminate the pain of eye irritation, not by the use of non-irritating ingredients, but by the addition of an ingredient to anesthetize the eyes so that the irritation caused to them is not transmitted to the pain centers. Unfortunately, the subject continues to suffer eye irritation.

An article by T. Schoenberg entitled "Formulating Mild Skin Cleaners", Soap/Cosmetics/Chemical Specialties, May 1983, p. 33, discloses various formulations of mild skin cleaners. Schoenberg recommends the use of sulfosuccinate half-esters as partial replacements of anionic surfactants, such as sodium lauryl sulfate, for reducing irritation. However, such replacement compounds are said to prevent significant irritation only when they are substituted in amounts on the order of 75%, which raises the cost of such cleansers to unduly high levels and reduces their foaming characteristics, significantly.

Accordingly, a need exists for cleaning compositions which are mild (non-irritating), yet have sufficient foaming for cleaning ability.

OBJECTS AND ADVANTAGES OF THIS INVENTION

It is an object of this invention to provide a means for reducing the concentration of anionic surfactants in skin and hair cleaning compositions without decreasing the foaming and cleaning characteristics of such compositions.

It is a further object of this invention to provide a means for reducing the irritation potential of anionic cleaning agents in skin and hair cleaning compositions.

It is a still further object of this invention to replace potentially irritating levels of anionic surfactants with alpha olefin/maleic anhydride terpolymers of predetermined compositional ranges.

It is yet another object of this invention to provide skin and hair cleaning compositions with satisfactory performance characteristics, but with significantly lower raw material costs.

SUMMARY OF THE INVENTION

This invention relates to cleaning compositions comprising at least one anionic surfactant, at least one alpha olefin/maleic anhydride terpolymer and an aqueous vehicle, such as water. The anionic surfactant has the capacity to provide foaming and cleansing properties to said composition and also has a tendency to irritate skin and eyes. The terpolymer is utilized in sufficient amounts to reduce the irritation potential of said composition without significantly reducing the foaming and cleansing properties thereof.

A wide variety of anionic surfactants may be utilized, with ammonium lauryl sulfate, ammonium lauryl ether sulfate, or mixtures thereof being preferred. The alpha olefin/maleic anhydride terpolymers, used in accordance with this invention, are those disclosed in Reexamination Certificate No. B1 4,358,573, the disclosure of which is herein incorporated by reference.

In more particular aspects, this invention relates to cleaning compositions comprising at least one anionic surfactant, at least one alpha olefin/maleic anhydride terpolymer, an aqueous vehicle, such as water, a pH control agent and a viscosity control agent.

It has been surprisingly found that the problem of user irritation caused by cleaning compositions containing anionic surfactants, such as ammonium lauryl sulfate and ammonium lauryl ether sulfate, is reduced without significantly interfering with either the foaming capability or cleaning performance of such compositions, when at least one alpha olefin/maleic anhydride terpolymer is used in combination with at least one anionic surfactant.

Additionally, it has been unexpectedly discovered that substantial amounts of alpha olefin/maleic anhydride terpolymer(s), for instance, as much as 50% by weight of the anionic surfactant, may be employed without appreciably interfering with the performance characteristics of the composition.

Cleaning compositions containing the above-stated terpolymers were tested in experimental salons against commercially-available, similarly-comprised compositions not containing these terpolymers. The products made in accordance with this invention showed a notable decrease in irritation as compared to the similarly-comprised commercial compositions, without a loss in the foaming or cleaning characteristics.

DESCRIPTION OF THE PREFERRED EMBODIMENTS

Skin and hair cleaning compositions in accordance with this invention include at least one anionic surfactant, at least one alpha olefin/maleic anhydride terpolymer and an aqueous vehicle, such as water. These are the essential ingredients of the cleaning compositions of the subject invention.

Anionic surfactants are used in cleaning compositions due to their high foaming and good cleaning characteristics. The type of anionic detergent utilized, in accordance with this invention, is not critical. It is a feature of commercially available anionic surfactants that they possess a tendency to irritate the keratinous tissue and mucous membranes which constitute, at least in part, the skin and eyes, respectively.

Suitable anionic surfactants which can be used in the scope of the subject invention include the saturated fatty acid salts, such as the alkali metal salts and particularly the sodium and potassium salts of saturated fatty acids having from about 12 to about 18 carbon atoms. Examples of such surfactants include the alkali metal salts of myristic acid, lauric acid, stearic acid, and the like and mixtures thereof.

Other suitable anionic surfactants which can be used in the scope of the subject invention include the alkali metal salts and particularly the sodium and potassium salts of alkyl aryl sulfonic acids and preferably the alkali metal alkyl benzene sulfonates wherein the alkyl group is a straight or branched chain group which contains from about 6 to about 18 carbon atoms. Examples of suitable such materials include the sodium and potassium salts of dodecyl benzene sulfonic acid, nonyl benzene sulfonic acid, undecyl benzene sulfonic acid, tetradecyl benzene sulfonic acid, hexadecyl benzene sulfonic acid, and the like, and mixtures thereof.

Further anionic surfactants which can be used in the scope of this invention include the salts and particularly the alkali metal and ammonium salts of sulfates of fatty alcohols having from about 12 to about 18 carbon atoms or mixtures thereof and the salts and particularly the alkali metal and ammonium salts of sulfates of ethoxylated fatty alcohols having from about 12 to about 18 carbon atoms and an average number of ethoxy groups from about 1 to 5. Examples of such materials include sodium sulfates of $C_{12}$ alcohols, sodium tridecyl alcohol sulfate, the sodium salt of ethoxylated lauryl sulfate with an average of about 1.5 ethoxy groups, ammonium lauryl sulfate, ammonium lauryl ether sulfate, and triethanolamine lauryl sulfate. Ammonium lauryl sulfate, ammonium lauryl ether sulfate and mixtures thereof are the preferred anionic surfactants.

Still further anionic surfactants which can be used in the scope of this invention include (1) alpha olefin sulfonates, for example, sodium $C_{14-16}$ olefin sulfonate and sodium $C_{16-18}$ olefin sulfonate; (2) sarcosinates, such as, sodium cocoyl sarcosinate, sodium lauroyl sarcosinate and triethanolamine lauroyl sarcosinate; (3) sulfosuccinates, for example, disodium cocamido MIPA sulfosuccinate, disodium oleamido PEG-2 sulfosuccinate, disodium laureth sulfosuccinate and laureth sulfosuccinate; and (4) isethionates, such as, sodium cocoyl isethionate, sodium isethionate and sodium lauroyl isethionate.

Mixtures of the various types of anionic surfactants may also be employed.

Typically, the anionic surfactants are employed in amounts from about 0.15 to 25 percent by weight of the total composition, with a range of about 8 to 15 percent by weight of the total composition being preferred. The amount of anionic surfactant utilized is not critical with higher and lower amounts being employed depending upon the other ingredients, additives and proportions thereof.

The alpha olefin/maleic anhydride terpolymers used in accordance with the teachings of this invention are disclosed in Reexamination Certificate No. B1 4,358,573, Issued, Nov. 15, 1983, which is incorporated herein by reference. These terpolymers typically comprise from about 49–60 mole percent maleic anhydride, from about 10–40 mole percent of at least one lower 1-alkene and from about 40–10 mole percent of at least one higher 1-alkene. The specific type of such alpha olefin/maleic anhydride terpolymer or terpolymers which is utilized in accordance with this invention, is not critical.

The first monomer of this terpolymer is a maleic anhydride, including methylmaleic anhydride, dimethyl maleic anhydride, fluoromaleic anhydride, and methylethyl maleic anhydride, with maleic anhydride being preferred. The second monomer of the terpolymer is a higher 1-alkene, i.e., a 1-alkene having at least 18 carbon atoms. These higher 1-alkenes may be pure materials or mixtures of various higher 1-alkenes. The preferred higher 1-alkenes are eicosene, $C_{20}$–$C_{24}$ mixtures, $C_{24}$–$C_{28}$ mixtures and $C_{30+}$ mixtures. The third monomer of the terpolymer is a lower 1-alkene having from 4 to 16 carbon atoms. The lower 1-alkenes that can be utilized in accordance with this invention include 1-butene, 1-pentene, 1-hexene, 1-heptene, 1-octene, 1-nonene, 1-decene, and the rest of the 1-alkenes up to 16 carbon atoms. Various mixtures of these lower 1-alkenes can be utilized. Preferred lower 1-alkenes are straight chain 1-alkenes having from 4 to 10 carbon atoms and mixtures thereof.

Typical alpha olefin/maleic anhydride terpolymers formed from $C_{10}$ or 1-decene; $C_{20-24}$ or 1-alkene mixture of $C_{20}$ to $C_{24}$ alkenes; $C_{30+}$ or 1-alkene mixture of $C_{30+}$ 1-alkenes and $MA_N$ (hereinafter maleic anhydride) are: 8 $C_{10}$/2 $C_{20-24}$/10 $MA_N$; 7 $C_{10}$/3 $C_{30+}$/10 $MA_N$; 5 $C_{10}$/5 $C_{20-24}$/10 $MA_N$; 2 $C_{10}$/8 $C_{20-24}$/10 $MA_N$ and 4 $C_{10}$/6 $C_{30}$/10 $MA_N$.

For the purpose of this invention, the terpolymer is employed in sufficient amounts to reduce irritation potential of said anionic surfactant-containing composition without reducing the foaming and cleansing properties of said composition. Accordingly, the alpha olefin/maleic anhydride terpolymer can comprise from about 0.1 to 18 percent by weight of the composition, with a range of about 2 to 5 percent by weight of the composition being preferred.

The amount of active solids including optional additives in the compositions of the invention typically varies from about 1% to 30%, with a range of about 10 to 20% being preferred.

In particular preferred aspects of this invention, various ratios of ammonium lauryl sulfate/ammonium ether sulfate surfactant blend(s) and the alpha olefin/maleic anhydride terpolymer(s) are effective as active agents in the cleaning compositions of this invention.

An aqueous vehicle, preferably water, is the final essential component of the subject compositions. Water makes up the remainder of the composition and is generally present at a level up to about 99%, preferably from about 80% to 90%. Substantially any purity water can be utilized in these compositions, although good manufacturing procedures usually require that the water be deionized and substantially free of major contaminants and impurities. Other water miscible carriers compatible with the surfactant and terpolymer of the invention can also be utilized with water.

In accordance with this invention, various other ingredients may be added to the aqueous compositions of anionic surfactant(s) and alpha olefin/maleic anhydride terpolymer(s). These ingredients typically include viscosity control agents, pH control agents, preservatives, fragrances, dyes, antibacterial agents, anti-dandruff ingredients, and the like.

A wide range of composition viscosities may be produced from combinations of the foregoing ingredients. Since it is desirable for skin and hair cleaning formulations to be thickened compositions, viscosity control agents are preferably used to help produce the desired viscosities. A thickened composition, e.g., a hair shampoo, typically makes the composition easier to handle and also helps to avoid the problem of shampoo dripping into the user's eyes. A variety of viscosity control agents may be utilized. For example conventional amide, betaine, hydrocolloid, amine oxide thickeners, in addition to inorganic salts may be employed. Examples of these viscosity control agents include polyoxyethylene, guar gum, methylcellulose, methylhydroxy cellulose, polypropyl hydroxyethyl cellulose, locust bean gum, hydroxypropyl guar gum, monoethanolamide, diethanolamide, and the like, and mixtures thereof.

The inorganic salts are preferred as viscosity control agents. It is believed that the primary function of an inorganic salt is to provide free electrolytes which increase the viscosity of the composition. Any compatible, non-toxic inorganic salt which is soluble in the composition of the present invention may be utilized. Examples of inorganic salts which may be utilized in accordance with the subject invention include sodium chloride, ammonium chloride, potassium chloride, lithium chloride, sodium citrate, potassium citrate, lithium citrate, ammonium citrate and mixtures thereof. Sodium chloride and ammonium chloride are preferred as viscosity control agents.

Depending on the desired clarity of the formulation, either opaque or clear, the combination(s) of terpolymer(s) and viscosity control agent(s) may be varied. For example, when a sodium cut (25% N.V.) of the terpolymer and the sodium chloride viscosity control agent is utilized, a relatively clear formulation results. On the other hand, when an ammonium cut (25% N.V.) of the terpolymer and the ammonium chloride viscosity control agent is utilized, an opaque formulation is obtained. The quantity of viscosity control agent utilized depends upon the desired viscosity of the final composition and the particular viscosity control agent(s) utilized. For example, with either sodium chloride or ammonium chloride a concentration range from about 0.01 to 10 percent by weight of the total composition can be employed, with from about 0.5 to 2 percent by weight of the total composition being preferred.

The preferred viscosity range for a skin cleaning formulation is from about 3,000 centipoise to about 6,000 centipoise for ease of application and stability in extremes of storage temperature. The preferred viscosity range for a hair cleaning formulation is from about 4,000 centipoise to about 15,000 centipoise. The viscosity is measured using a Brookfield viscometer equipped with a number LV4 spindle set at 30 rpm.

A further useful ingredient used in accordance with this invention is a pH control agent. The type pH control agent and quantity used is be chosen to ensure maximum efficiency of the cleaning composition, i.e., without damage to the hair or irritation to the eyes or skin. A primary purpose of the pH control agent is to lower the pH of the resultant composition. Various organic or inorganic acids may typically be utilized for this purpose. The organic acids that may typically be employed include citric acid, malic acid, acetic acid, ascorbic acid, succinic acid, and the like, and mixtures thereof. Inorganic acids that typically can be used include hydrochloric acid, boric acid, phosphoric acid, and the like, and mixtures thereof. Additionally, these acids tend to have a buffering effect within the desired pH range when used in combination with the anionic surfactants and the inorganic salts described above. The preferred acid for pH control is citric acid.

The pH of skin cleaning formulations, in accordance with this invention, can range from about 3.0 to 7.0, with a range of about 4.0 to 6.5 being preferred, and about 5.0 to 6.0 even more preferred. The pH of hair cleaning formulations, in accordance with this invention, can range from about 3.5 to 7.0, with about 5.0 to 6.5 being preferred. The pH of skin varies from aoout 5.0 to 6.0 and accordingly, to minimize irritation, the composition pH should approximate that of skin.

As seen from the following formulation method, the addition of acid(s) decreases the alkalinity of the formulation from the alkaline ranges imparted by the addition of the surfactant and terpolymer blend(s) to the desired pH range(s) of the final formulation. The reduction of alkalinity is an important step in preventing loss of free ammonia thereby keeping the polymeric material in solution.

Various other additives are conventionally added to cleaning compositions, such as preservatives, fragrances, dyes, antibacterials, anti-dandruff ingredients, and the like.

One method of ingredient incorporation for compositions, in accordance with this invention, and as used to formulate the examples, is as follows:

PREPARATION EXAMPLE

To the total amount of deionized water in the product, add the surfactant or surfactant blend followed by the addition of the alpha olefin/maleic anhydride terpolymer. The pH of this mixture is typically between about 7 and 10. Next, the pH control agent is added to this mixture to reduce the alkalinity and thereby adjust the pH to the desired level. Any other additional ingredients can then be added at this point. These include preservatives, dyes, fragrance, etc. Finally, the viscosity control agent is added to obtain the desired viscosity. The sequence of ingredient incorporation is not critical to the subject invention and the subject compositions can be formulated using any known manufacturing process.

The compositions of the present invention may be illustrated by way of the following examples which are presented for illustration and not intended to be limiting:

EXAMPLE 1

A clear skin cleansing composition of the invention was prepared by the process set forth in the Preparation Example. That composition had the following formulation:

| Ingredient | Amount (grams) |
| --- | --- |
| ammonium lauryl sulfate/ammonium lauryl ether sulfate | 35 |
| alpha olefin/maleic anhydride terpolymer (sodium cut) | 15 |
| citric acid | 1 |
| formalin preservative | 0.25 |
| fragrance and color | trace |
| sodium chloride | 1.5 |
| deionized water | q.s. |

The composition was applied to the skin as a hand soap. The composition was perceived to possess similar lather and skin feel characteristics, such as cleanliness and softness, as conventional liquid hand soap cleansers. Additionally, both skin and eye irritation were substantially reduced as measured in animal tests by use of the composition of Example 1 as compared to a conventional liquid hand soap cleanser, i.e., one containing the anionic surfactants without the alpha olefin/maleic anhydride terpolymer.

EXAMPLE 2

An opaque skin cleansing composition of the invention was prepared by the process set forth in the Preparation Example. That composition had the following formulation:

| Ingredient | Amount (grams) |
| --- | --- |
| ammonium lauryl sulfate/ammonium lauryl ether sulfate | 35 |
| alpha olefin/maleic anhydride terpolymer (ammonium cut) | 15 |
| citric acid | 1 |
| formalin | 0.25 |
| fragrance and color | trace |
| ammonium chloride | 1.5 |
| deionized water | q.s. |

Similar results as shown Example 1 above were obtained.

EXAMPLE 3

An opaque hair cleansing composition of the invention was prepared by the process set forth in the Preparation Example and had the following formulation:

| Ingredient | Amount (grams) |
| --- | --- |
| ammonium lauryl sulfate/ammonium lauryl ether sulfate | 35 |
| alpha olefin/maleic anhydride terpolymer (ammonium cut) | 15.40 |
| citric acid | 0.80 |
| Kathon CG | 0.01 |
| fragrance | 0.5 |
| color (yellow #10 and Blue #1) | 1.05 |
| ammonium chloride | 0.75 |
| deionized water | 40.214 |

In comparison with a conventional hair cleansing composition containing anionic surfactants without alpha olefin/maleic anhydride terpolymers, the above example compared favorably in foam ability and foam stability. The formulation of Example 3 produced no skin irritation and significantly reduced the eye irritation in animal tests as compared to the conventional hair cleansing composition.

In Examples 1 through 3, the alpha olefin/maleic anhydride terpolymer used in the sodium or ammonium hydroxide-cut solution (25% N.V.) is a blend of 0.5% $C_{10}$/0.5% $C_{18-20}$/1% $MA_N$ (mole %) in a ratio of 1 mole percent alpha olefin to 1 mole percent maleic anhydride. The ratio of ammonium lauryl sulfate to ammonium lauryl ether sulfate is 50:50 and the blend consists of 28% solids in an aqueous solution.

The invention is not to be limited except as set forth in the following claims.

What is claimed is:

1. A cleaning composition comprising:
   (a) at least one anionic surfactant having foaming and cleansing properties and a tendency to irritate sensitive tissues in an amount of 0.15 to 25% by weight of the composition;
   (b) at least one alpha maleic anhydride terpolymer containing about 49–60 mole percent maleic anhydride, about 10–40 mole percent of at least one lower 1-alkene having from 4–16 carbon atoms, and about 40–10 mole percent of at least one higher 1-alkene having at least 18 carbon atoms in an amount of 0.1 to 18% by weight of the composition, said ingredient in amount so as not to reduce the foaming and cleaning properties of said composition; and
   (c) an aqueous vehicle in an amount up to 99% by weight of the composition.

2. A composition according to claim 1 wherein said anionic surfactant is ammonium lauryl sulfate, ammonium lauryl ether sulfate, or mixtures thereof.

3. A composition according to claim 1 wherein said lower 1-alkene is selected from a group consisting of 1-butene, 1-pentene, 1-hexene, 1-heptene, 1-octene, 1-nonene, 1-decene, and mixtures thereof.

4. A composition according to claim 1 wherein said higher 1-alkene is selected from a group consisting of 1-alkenes having at least 18 carbon atoms, and mixtures thereof.

5. A composition according to claim 1 which further comprises an acid pH control agent.

6. A composition according to claim 5 wherein said acid is selected from a group of organic acids consisting of citric acid, malic acid, acetic acid, ascorbic acid, succinic acid, and mixtures thereof.

7. A composition according to claim 5 wherein said acid is selected from a group of inorganic acids consisting of hydrochloric acid, phosphoric acid, boric acid, and mixtures thereof.

8. A composition according to claim 1 which further comprises a viscosity control agent.

9. A composition according to claim 8 wherein said viscosity control agent comprises an inorganic salt or mixtures thereof.

10. A composition according to claim 9 wherein said inorganic salt is selected from a group consisting of sodium chloride, ammonium chloride, potassium chloride, lithium chloride, sodium citrate, potassium citrate, lithium citrate, ammonium citrate, and mixtures thereof.

11. The composition according to claim 1 wherein said anionic surfactant is present in amounts from about 8 to 15 percent by weight of the composition and said alpha olefin/maleic anhydride terpolymer is present in amounts from about 2 to 5 percent by weight of the composition.

12. The composition according to claim 5 wherein said pH control agent is present in sufficient amounts to maintain a composition pH from about 3.0 to 7.0.

13. The composition according to claim 5 wherein said pH control agent is present in sufficient amounts to maintain a composition pH from about 0.5 to 6.5.

14. The composition according to claim 8 wherein said viscosity control agent is present in amounts from about 0.01 to 10 percent by weight of the composition.

15. The composition according to claim 8 wherein said viscosity control agent is present in amounts from about 0.5 to 2 percent by weight of the composition.

* * * * *